United States Patent [19]
Higo et al.

[11] Patent Number: 6,104,950
[45] Date of Patent: Aug. 15, 2000

[54] PLASTER STRUCTURE FOR IONTOPHORESIS

[75] Inventors: Naruhito Higo; Kenji Mori; Katsuhiro Nakamura, all of Tsukuba, Japan

[73] Assignee: Hisamitsu Pharmaceutical Co., Inc., Tsukuba, Japan

[21] Appl. No.: 09/011,459
[22] PCT Filed: Aug. 14, 1995
[86] PCT No.: PCT/JP95/01614
    § 371 Date: Jun. 3, 1998
    § 102(e) Date: Jun. 3, 1998
[87] PCT Pub. No.: WO97/06847
    PCT Pub. Date: Feb. 27, 1997
[51] Int. Cl.[7] ............................................. A61N 1/30
[52] U.S. Cl. ................................. 604/20; 607/152
[58] Field of Search ..................... 604/20; 602/47, 602/48, 58; 128/114.1; 607/152, 153

[56] References Cited

U.S. PATENT DOCUMENTS

| | | | |
|---|---|---|---|
| 4,177,871 | 12/1979 | Bevilacqua | 128/802 |
| 5,232,438 | 8/1993 | Theeuwes et al. | 604/20 |
| 5,697,896 | 12/1997 | McNichols et al. | 604/20 |
| 5,738,647 | 4/1998 | Bernhard et al. | 604/20 |
| 5,817,044 | 10/1998 | Evers et al. | 604/307 |

FOREIGN PATENT DOCUMENTS 3-504343A  9/1991  Japan.

*Primary Examiner*—Sharon Kennedy
*Attorney, Agent, or Firm*—Andrew C. Aitken

[57] ABSTRACT

Plaster structures for iontophoresis are disclosed for the administration of drugs through skin and mucous membranes. The devices provide for the stable retention and storage of a predetermined amount of a physiologically active agents until the device is applied to a patient. The devices include an electrically conductive medicinal substance storing layer which contains physiologically active agents, and a non-permeable backing layer which covers the medicinal substance storing layer. An electrode passes through the backing layer where it makes contact with the medicinal substance storing layer. On the opposite side of the storing layer a non-permeable protective layer is provided which a has a portion adapted to be removed to allow access to the medicinal substance storing layer. This protective layer supports the medicinal substance layer and, on the opposite side, is provided with an adhesive agent layer. The adhesive agent is protected by a laminate layer. The device is designed so that when the laminate layer is removed to expose the adhesive agent, a potion of the protective layer is also removed allowing the medicinal substance storing layer to be brought into contacted with skin or a mucous membrane.

26 Claims, 6 Drawing Sheets

FIG. 8

PLASTER STRUCTURE FOR IONTOPHORESIS

TECHNICAL FIELD

This invention relates to a plaster structure for iontophoresis which is preferably applied for a treatment through skins and mucous membranes. More particularly, this invention relates to a plaster structure for iontophoresis used for administering medicines through skins, mucous membranes under a principle of iontophoresis, wherein the plaster structure for iontophoresis is superior in stability for keeping physiologically active agents and capable of restricting a relative action between the physiologically active agents and adhesive agent layer during its application.

BACKGROUND ART

Generally when the physiologically active agents are absorbed into a physical body through skins or mucous membranes, medicinal substances administered through skins or mucous membranes have been studied positively due to the fact that the medicinal substances of this type have some advantages that they show a convenience in administering, keeping a blood concentration and a capability of avoidance of side effects of physiologically active agents against a digestive canal or the like as compared with an oral administering. In particular, as a local administering method which is effective for promoting absorption of physiologically active agents through skins or mucous membranes, iontophoresis has been noticed.

Iontophoresis is a kind of method for promoting physical absorption of physiologically active agents, wherein a certain voltage is applied to either skins or mucous membranes to cause the physiologically active agents to generate electrophoresis and further physiologically active agents to be administered through skins or mucous membranes.

A usual type of plaster structure for iontophoresis has a configuration in which a medicinal substance storing layer for use in storing physiologically active agents and the electrodes are combined to each other and various kinds of additive agents as required in addition to physiologically active agents of a pre-designed specified amount are enclosed in the medicinal substance storing layer in order to administer a controlled amount of physiologically active agents continuously to a physical circulating system for a specified period of time so as to keep a stable medical effect.

As the plaster structure for iontophoresis satisfying these requirements, various kinds of structures have been disclosed in the gazettes of Japanese Patent Laid-Open No. Sho 62-268569 or 63-102768, Japanese Utility Model Laid-Open No. Sho 64-50844, Japanese Utility Model Laid-Open No. Hei 2-53757 and Japanese Patent Laid-Open No. Hei 3-45271 or the like.

However, it has been found that these prior art configurations described above have some problems that either the physiologically active agents or additive agents or the like are leaked out of the medicinal substance storing layer or dispersed and immersed into the adhesive agent layer by a time in which the plaster structure for iontophoresis is applied to a patient, resulting in that the actual amount of substances is reduced by less than the predetermined amount of physiologically active agents and medical effectiveness or durability or reliability is reduced. In addition, the physiologically active agents or additive agents or the like are immersed into the adhesive agent layer, resulting in that a problem occurred that an adhering force of the adhesive agent to skins or mucous membranes was weakened and the agent might easily be peeled off. As per the item in which a pressure-sensitive adhesive agent layer was provided at a releasing surface for the physiologically active agents, it had a problem that a serious influence was applied to a continuous and uniform application of the physiologically active agents under a mutual action between the physiologically active agents or additive agent and the adhesive agent layer when the item was applied to a patient or the adhesive agent layer was deteriorated or its durability was deteriorated.

This invention resolves the aforesaid problems of the prior art and it is an object of this invention to provide a plaster structure for iontophoresis in which a predetermined amount of physiologically active agents initially set can be stably kept or held without any loss until it is applied to a patient and when the item is applied to the patient, the predetermined amount of physiologically active agents initially set can be applied continuously to an entire body of the patient and concurrently a mutual action between the physiologically active agents or additive agents and the adhesive agent is prevented, an adhering power of the adhesive agent is kept and it may not be peeled off during its application.

DISCLOSURE OF THE INVENTION

In order to accomplish the object described above, the plaster structure for iontophoresis of the present invention has the following configuration.

The plaster structure for iontophoresis according to a first embodiment is comprised of an electrical conductive medicinal substance storing layer containing physiologically active agents, a backing layer covering the medicinal substance storing layer with an electrode installed therein and which is non-permeable against the physiologically active agents, a protection layer supporting the medicinal substance storing layer and which is non-permeable against the physiologically active agents, an adhesive agent layer laminated on the other surface of the protection layer, and a liner layer laminated on the other surface of the adhesive agent layer.

An alternative embodiment of the plaster structure for iontophoresis has a configuration in which the adhesive agent layer is comprised of a pressure-sensitive adhesive agent or gelation adhering agent which is superior in a skin adhering characteristic and/or a mucous membrane adhering characteristic.

A further embodiment includes a configuration in which a spacer film layer which is permeable against the physiologically active agents is provided between the medicinal substance storing layer and the protection layer.

A further contemplated embodiment has a configuration in which the protection layer is provided with a notch formed around a side part of a contact surface with the medicinal substance storing layer.

In yet a further contemplated embodiment the plaster structure for iontophoresis has a configuration in which the protection layer is comprised of two or more synthetic resin layers.

A further contemplated embodiment has a configuration in which a part corresponding to a section of the protection layer to be broken and removed at the surface of the liner layer is not processed for its peeling and only the other portions are processed for peeling.

A further embodiment includes a configuration in which the backing layer, the spacer film layer, the adhesive agent layer and the liner layer are formed to be larger than the medicinal substance storing layer and the protection layer, the backing layer around a peripheral edge part of the medicinal substance storing layer and the spacer film layer are heat sealed and further the protection layer is formed to be larger than the heat seal section.

In this case, as the physiologically active agents, all kinds of medicinal substances for medical treatment in major fields of medical treatment which are water soluble or dispersed in water or their combinations are included and the following substances are applied as examples but are not limited to them: anesthetics, anodynes, anti-anorexic medicines, vermicides, anti-asthmatic medicines, anti-convulsion medicines, anti-diarrhea medicines, anti-migraine medicines, anti-intoxication medicines, anti-emesis medicines, anti-tumor medicines, anti-Parkinson's disease medicines, anti-urtication medicines, antifebriles, sympathetic nerve agonists, xanthines, cardiovascular medicines such as potassium passage antagonist, beta-antagonists, anti-arrhythmic medicines, hypotensives, diuretics; vasodilators including those for the entire body, coronary vessels, peripheral capillaries; central nervous system stimulants, cough and cold medicines, decogestants, diagnostic agents, hormones, soporifics, anti-immune medicines, muscle relaxants, parasympathetic nerve inhibitors, parasympathetic nerve acting medicines, mind stimulants, sedatives, tranquilizers, anti-inflammation medicines, anti-arthritis medicines, antispasmodic, anti-depressants, anti-mental disease medicines, anti-vertigo medicines, anti-anxiety medicines, anesthetic antagonists, anti-Parkinson's decease medicines, anti-cancer medicines, immunizing agents, anti-viral medicines, antibiotics, anorexic agents, emesis sedatives, anti-choline agents, antihistamines, anti-migraine medicines, hormone preparations, contraceptives, anti-thrombosis medicines, diuretic, blood pressure reducing medicines, cardiac vessel medicines or the like.

As examples of respective physiologically active agents, following substances are applicable: steroids such as estradiole, progesterone, norgestrel, levonorgestrel, norethindrone, medroxyprogesterone acetate, testosterone, and their ester; derivatives of nitro-compounds such as nitroglycerin and isosorbide dinitrade, nicotine, chlorphenylamine, terfenadine, triprolidine, hydrocortisone, oxicam derivatives such as piroxicam, ketoprofen, mucopolysaccharase such as thiomucarse, buprenorphine, fentanyl, naloxone, codeine, lidocaine, dihydroergotamine, pisotyline, salbutamol, terbutaline, prostaglandin such as misoprostol, enprostil, omeprazole and imipramine, benzamide such as metoclopramine, scopolamine; peptides such as growth releasing factor and somastatin, clonidine, dihydropyridine such as nifedepin, verapamil, ephedrine, pindolol, metoprolol, spironolactone, nicardipine hydrochloride, calcitriol; thiazide such as hydrochlorothiazide, flunarizine, sydnone imine such as molsidomin, sulfated polysaccharide such as heparin fraction and protein, and peptide such as insulin and its homology; calcitoning and its homology such as elcatomin, protamine, glucagon, blobulin, angiotensin I, angiotensin II, angiotensin III, riblessin, vasopressin, somatostatin and its homology, growth hormone and oxytocin; and if necessary, salts of acids and bases pharmaceutically compatible with their compounds. Other effective medicinal substances are preferably as follows but are not limited to them; anesthetics, hormones, protein, pain-killers, or other low molecular cations. More preferable ones include but are not limited to; peptide or insulin of the peptide family, calcitonin, calcitonin-related gene peptide, vasopressin, desmopressin, protirelin (TRH), adrenal cortex exciting hormone (ACTH), corpus luteum forming hormone releasing hormone (LH-RH), growth hormone releasing hormone (GRH), nerve growth factors (NGF) and other release factors, angiotensin, parathyroid gland hormone (PTH), corpus luteum forming hormone (LH), prolactin, serum-like sex gland exciting hormone, pituitary gland hormone (e.g. HGH, HMG, HCG), growth hormone, somatostatin, somatomedin, glucagon, oxytocin, gastrin, secretin, endorphin, enkephalin, endocering, cholecystkinin, neurotensin, interferon, interleukin, transferein, erythropoiten, superoxide dismutase (SOD), filgrastim (G-CSF), vasoactive intestinal polypeptide (VIP), muramyl dipeptide, cortiocotropine, urogastrone, atrium-acting sodium diuretic peptide (h-ANP).

As major requirements for the effective physiologically active agents, it is necessary that they are electrically charged, they may be modified to carry an electrical charge or they may form a complex with other compounds through a hydrophobic mutual action, for example, and the complex may hold the electrical charging, although it is sometimes found that an electrical charging is not required. As a proper selection of the effective physiologically active agents for iontophoresis, it includes a selection based on a respective conductivity and an easiness in which the physiologically active agents may freely be moved in the solution as required in the case that an electrical current is applied. It is also possible that two or more kinds of these physiologically active agents are applied together as required. In addition, as the physiologically active agents, they may be enclosed in the medicinal substance storing layer as compound of derivatives of ester, compound of derivative of amide or compound of derivative of acetar or inorganic salt or organic salt allowed in view of medical treatment.

A mass of the physiologically active agent contained in the medicinal substance storing layer is determined for every physiologically active agents in such a way that an effective blood concentration set in advance when the substance is actually applied to a patient may be attained for an effective period of time and then both a size of the backing layer of the plaster structure for iontophoresis and an area of the physiologically active agents releasing surface are correspondingly determined.

It is satisfactory if the medicinal substances contained in the medicinal substance storing layer have a sufficient electrical conduction and any type of medicinal substances such as aqueous solution, suspension, ointment, gelation or cream or the like may be applied.

In addition, it is also possible to enclose in the plaster, a paper material such as a water absorbing paper or the like, a cloth material such as a gauze or the like, a fibrous material such as an absorbent cotton or the like, a continuous foamed synthetic resin material, a sponge such as aqueous absorbing resin or the like and an aqueous absorbing material for immersing medicinal liquid such as a porous material or the like.

As the additive agents for the physiologically active agents, it is also possible to add as required, solvents such as water, ethanol etc.; emulsifiers such as phosphatide acid derivatives, lecithin, cephalin, polyalkylene grycol etc.; absorbing promoters such as methyl laurate, methyl caprate, azone, oleic acid, 1-menthol, limonene, oil of peppermint etc.; dissolution agents or dissolution promotors such as crotamiton, ethylene glycol, diethylene glycol, triethylene glycol, propylene glycol, polyethylene glycol, polypropylene glycol, dimethyl sulfoxide, dimethylformamide, dimethylacetamide, dimethyllaurylamide, isosorbitol, olive oil, castor oil, squalene, and lanolin etc.; viscosity enhancers such as cellulose acetate, methyl cellulose, hydroxylmethyl cellulose, hydroxypropylemethyl cellulose, sodium carboxymethyl cellulose, stearyl alcohol etc.; stimulant reducers such as glycerine mono-oleic acid, glycerine monolaurate, sorbitan monolaurate etc.; hydrophilic and water absorbing macromolecular substances such as karaya gum, tragacanth gum, polyvinyl alcohol and its partial saponified compounds, polyvinyl pyrolidone, poly (meta) acrylate, polyacrylic acid and its sodium salt, polyacrylamide and their local hydrolytic products; plasticizers such as glycerin or the like.

These additives are determined in such a range as one in which a type and a concentration assumed to be the most-suitable one for every physiologically active agents are effective in view of medical treatment and allowed in view of medicinal substances.

In addition, as required, it is also possible to add some electrolytic substances such as sodium chloride, sodium carbonate and potassium citrate or the like.

As the backing layer, material which is not permeable at least against the physiologically active agents is used in order to prevent a leakage of physiologically active agents or the additives or the like. As an example of this material, either a single layer or a plurality of layers of a film or a sheet of synthetic resin is used while it is made of the following substances such as polyethylene, polypropylene, polyethyleneterephtarate, poly-vinyl chloride, poly-vinylidene chloride, plasticizing copolymer of vinyl acetate, copolymer of plasticizing copolymer of vinyl acetate and vinyl chloride, polyamide, cellophane, cellulose acetate, ethyl cellulose or the like. In addition, as these films or sheets made of synthetic resin, the products laminated with aluminum foil or vapor deposited with aluminum or coated with ceramics or the products having these materials laminated may also be used.

Electrodes for iontophoresis are installed within the backing layer so as to be contacted with the medicinal substance storing layer. Although a method for installing or feeding the electrodes in the backing layer is not particularly limited to this method disclosed, it is preferable that they are integrally formed by a circuit printing operation due to the fact that stability in quality can be improved.

The backing layer has a recess for use in putting the medicinal substances as required and holding it therein. Although both a shape of the backing layer and a shape of the recess are not limited in particular, it is generally preferable that the shape is formed into a circular shape or an ellipse or a substantial rectangular shape.

As materials for the electrode, silver, silver chloride, platinum, platinum black, aluminum, iron, lead, carbon, electrical conductive rubber and electrical conductive resin or the like can be applied. In addition, according to a certain type of electrode, in order to prevent a bad influence of deterioration or the like caused by physiologically active agents and improve durability of the electrode, the electrode protection layer made of conductive material may also be partially or entirely laminated and formed on the medicinal substance storing layers.

As the protection layer, it must have a non-permeable characteristic against all the physiologically active agent substances contained in the medicinal substance storing layer. In addition, generally, it is preferable to select such materials as one which can be heat sealed against the backing layer and the spacer film layer. More practically, some materials listed in the paragraph about the materials for backing layer are used in a single layer or in a plurality of laminated layers. Further, in place of making a heat seal between the backing layer and the protection layer and/or the spacer film layer, they may be adhered with adhesive agent.

As the adhesive agents, pressure sensitive adhesive or gel-like gluing agent will work satisfactorily in the adhesive layer. This pressure sensitive adhesive or gel-like gluing agent can support the iontophoresis plaster structure on the surface of the patient's skin or mucous membrane and when a notch is provided on the protective layer, the agent is satisfactory if it has a sufficient adhering strength for breaking the protective layer at the notch section when the liner layer is peeled off and allowed in view of the physical characteristics of skin and mucous membrane treatments. For instance, acrylic adhesives such as poly-2-ethylhexylacrylate, methacrylic adhesives such as polybutylmetacrylate, silicone adhesives such as polydimethylsiloxane, rubber adhesives such as polysioprene rubber, polyisobutylene rubber, polybutadiene rubber, natural rubber, polyvinyl alcohol, gelatin, polyvinyl pyrrolidone, carboxyvinyl polymer, and poly-sodium acrylate and its crosslinked products, sodium alginate and its crosslinked products, cellulose derivatives etc. can be used.

As the liner layer, either films or sheets of synthetic resin such as plastic films and cellulose films or the like are preferably used. As required, some substances which are not permeable against the pysiologically active agents or additives and the like are applied. In general, it is possible to use a complex layer having laminated either a film or a sheet in which the section corresponding to a part of the protection layer to be broken and peeled off is not processed for its removal and only other remaining sections are processed for removal through processing with silicone or fulorocarbon or the like, or laminated either a film or a sheet in which a part similar to a section of the protection layer is broken or removed or a part punched to be smaller than the former section is removed.

As the spacer film layer which is permeable against the physiologically active agents or additives, the layer which is permeable against the physiologically active agent or additives capable of being adhered to the aforesaid backing layer is generally used, and for example, a porous film or sheet or the like made of polyetylene, polyolefin such as polypropylene or the like, polyester, polycarbonate, poly-vinyl chloride, polyamide, polyimide, polyacrylonitrile, polystylene derivatives, copolymer of etylene-vinyl acetate, copolymer of etylene-polyvinyl alcohol, fluororesin, acrylic resin, epoxy resin, cellulose and foamed polyisoprene rubber or the like is used.

The plaster structure for iontophoresis of the present invention is connected to a current generating circuit and a power supply device, although the current generating circuit and the power supply device can be separated from the plaster structure for iontophoresis and connected with a connection cord or the like and they may be integrally assembled with the plaster structure.

In the case that the plaster structure is used while they are being integrally assembled, any kind of battery cells can be applied if they are small in size and light in weight, although normally a button-shaped battery cell and a sheet-like battery cell are preferably used.

A current value required in the plaster structure for iontophoresis is normally 0.001 to 10 $mA/cm^2$, preferably 0.01 to 1 $mA/cm^2$, an output of the battery cell is dependent on a contact area between a patient's skin and the plaster structure for iontophoresis and approximately 0.5 to 18 V or so, and preferably 3 to 9 V. Accordingly, as required, some amplifying elements having these several light weight battery cells arranged or laminated or changed into chips can be used in their combined states.

In addition, it is also applicable that a constant current element or a light emitting element for displaying an electrical energization or the like is added as required.

The plaster structure for iontophoresis of the present invention can be used at an anode or a cathode in compliance with a characteristic of the physiologically active agents. In addition, as required, it may also be applicable to both anode and cathode in concurrent manner.

With such an arrangement as above, since the medicinal substance storing layer is completely sealed by the backing layer and the protection layer, it is possible to prevent a leakage of the physiologically active agents or additives or the like. In the case that a notch is formed around the side part of the abutting surface of the protection layer against the medicinal substance storing layer, a mere peeling-off of the liner layer enables a releasing passage for the physiologically active agents to be easily formed. Further, in the case that a vertical slit is formed at the notch part, a simple and easy operation enables the releasing passage for the physiologically active agents to be positively formed by a simple operation.

In the case that the spacer film layer is formed between the medicinal substance storing layer and the protection layer, it is also possible to control an administering amount of the physiologically active agents. In the case that the protection layer or the liner layer or the backing layer is comprised of two or more synthetic resin layers, it is also possible to enforce an adhering characteristic and a barrier characteristic, attain a superior mechanical strength and increase a durability.

In the case that the liner layer is formed with the removal processing part, a connecting force at each of the laminated part and the removal processing part is remarkably different from each other, so that pulling of the removal processing part enables the releasing passage for the physiologically active agents to be easily formed.

In the case that the backing layer, the spacer film layer, the adhesive agent layer and the liner layer are larger in size than the medicinal substance storing layer and the protection layer, the backing layer at the peripheral part of the medicinal substance storing layer and the spacer film layer are adhered to each other by the heat seal or the like, and the protective layer is formed to be larger than the adhering part such as the heat seal or the like, mere pulling-off of the liner layer enables the releasing passage of the physiologically active agents to be easily formed even if the protection layer is not formed with the notch part.

PREFERRED EMBODIMENTS OF THE INVENTION

Referring now to the drawings, some preferred embodiments of the present invention will be described as follows.

Preferred Embodiment 1

Figure 1:
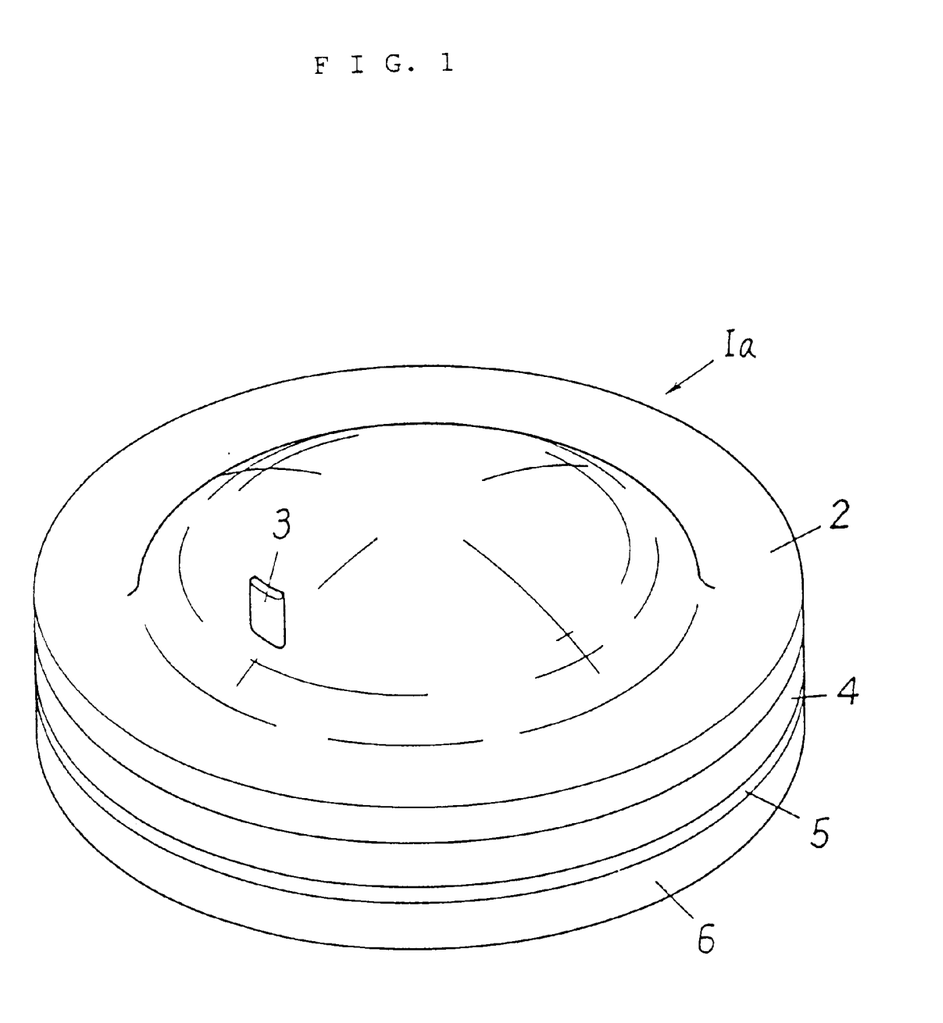
FIG. 1 is a perspective view for showing a plaster structure for iontophoresis in a first preferred embodiment of the present invention.
Figure 2A:
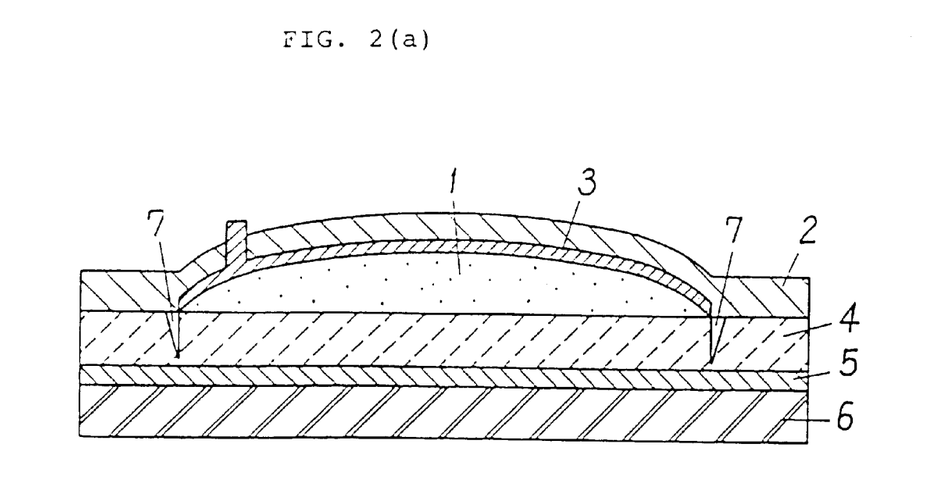
FIG. 2(a) is a longitudinal view in section for showing a substantial part of a central section of the plaster structure for iontophoresis of the first preferred embodiment of the present invention.
Figure 2B:
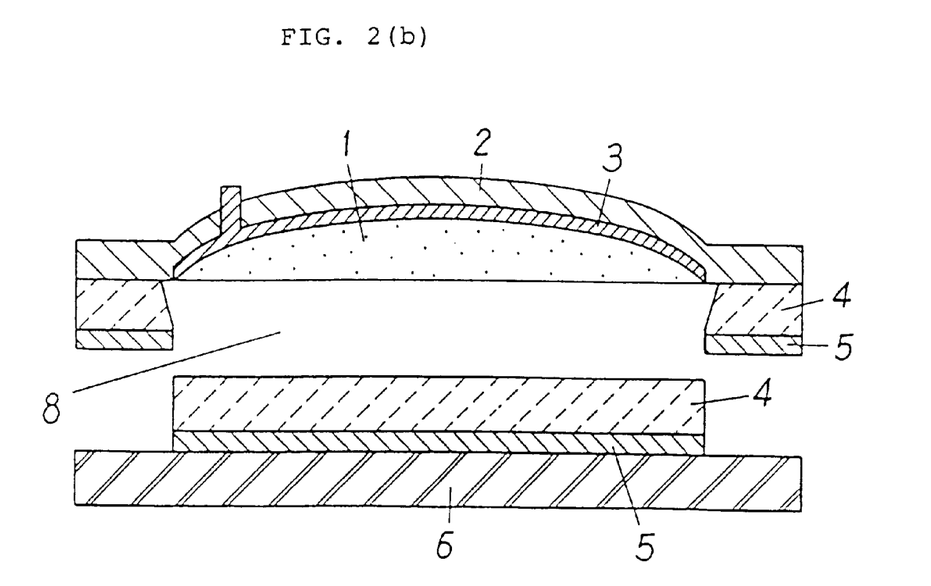
FIG. 2(b) is a longitudinal view in section for showing a substantial part of a central section to illustrate a state in which a releasing passage for physiologically active agents of the plaster structure for iontophoresis of the first preferred embodiment of the present invention is formed.

FIG. 1 is a perspective view for showing a plaster structure for iontophoresis in a first preferred embodiment of the present invention, FIG. 2(a) is a longitudinal view in section for showing a substantial part of a central section of the plaster structure for iontophoresis of the first preferred embodiment of the present invention, and FIG. 2(b) is a longitudinal view in section for showing a central part to illustrate a state in which a releasing passage for physiologically active agents of the plaster structure for iontophoresis of the first preferred embodiment of the present invention is formed.

Reference symbol Ia denotes a plaster structure for iontophoresis of the first preferred embodiment; 1 denotes an electrical conductive medicinal substance storing layer having first upper and second lower surfaces and containing physiologically active agents or additives or the like; 2 denotes a backing layer covering the medicinal substance storing layer 1; 3 denotes an electrode for iontophoresis internally installed at the inner wall of the backing layer 2 by a circuit printing, contacted with the medicinal substance storing layer 1 and electrically energizing the medicinal substance storing layer 1; 4 denotes a protection layer made of polyester for supporting at its first upper surface the medicinal substance storing layer 1 which is not permeable against the physiologically active agents or additives closely contacted at its circumferential edge to the backing layer 2 by various kinds of adhering methods (preferably, its peeling may not be attained and a permanent heat seal is desired); 5 denotes an adhesive agent layer made of pressure-sensitive adhesive agent such as acrylic resin adhesive agents or gelation gluing agents such as polyvinyl alcohol or the like indicating a preferable adhesion characteristic laminated over an entire second lower surface of the protection layer 4 against either a skin or a mucous membrane; 6 denotes a liner layer laminated over an entire second lower surface of the adhesive agent layer 5 and formed with a peeling-off knob part at its side as required; 7 denotes a notch part formed at an opposing first surface of the protection layer 4 against the medicinal substance storing layer 1 and around the medicinal substance storing layer 1; and 8 denotes a releasing passage for physiologically active agents released by a peeling-off of the liner layer 6.

Figure 3A:
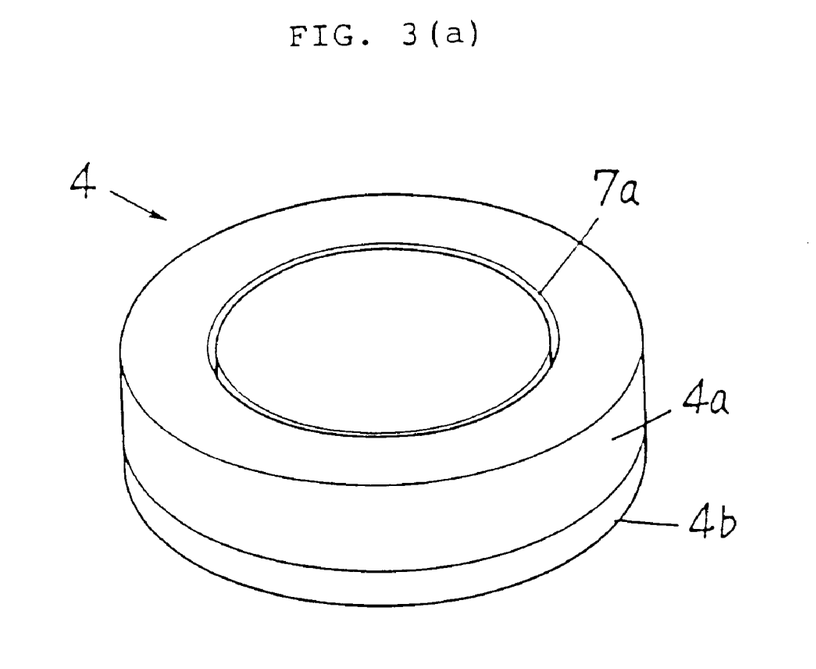
FIG. 3(a) is a perspective view for showing a protection layer having a notch part formed by a die cut blade.
Figure 3B:
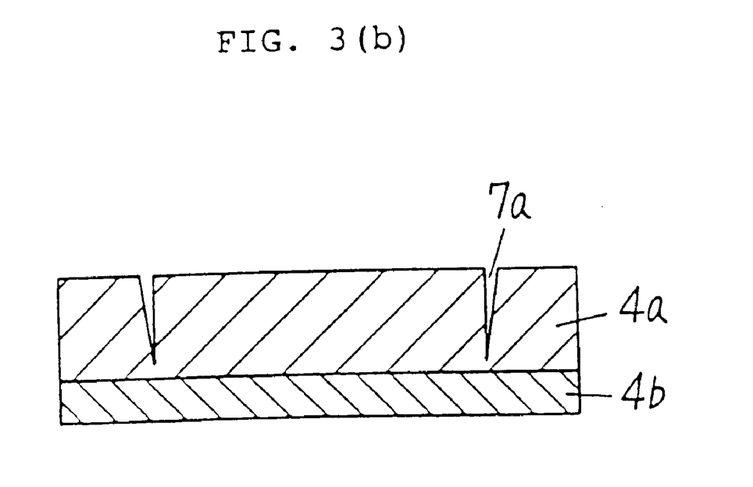
FIG. 3(b) is a sectional view for showing a substantial part at the central section.
Figure 4A:
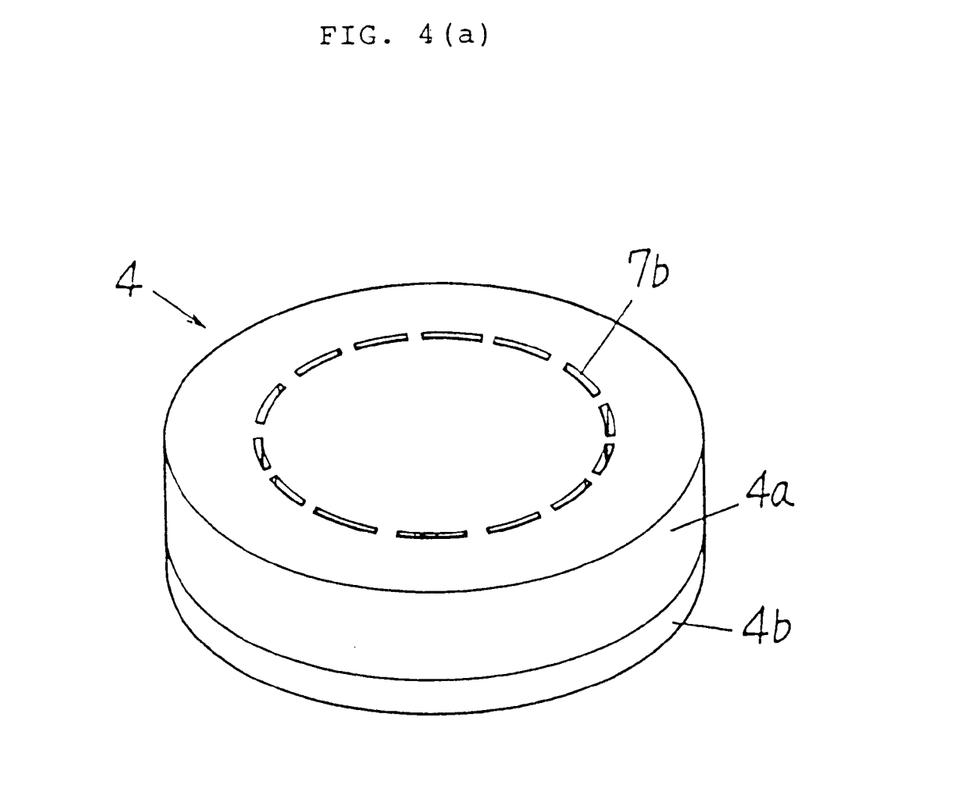
FIG. 4(a) is a perspective view for showing the protection layer having a perforated notch section of one of the other examples of application.
Figure 4B:
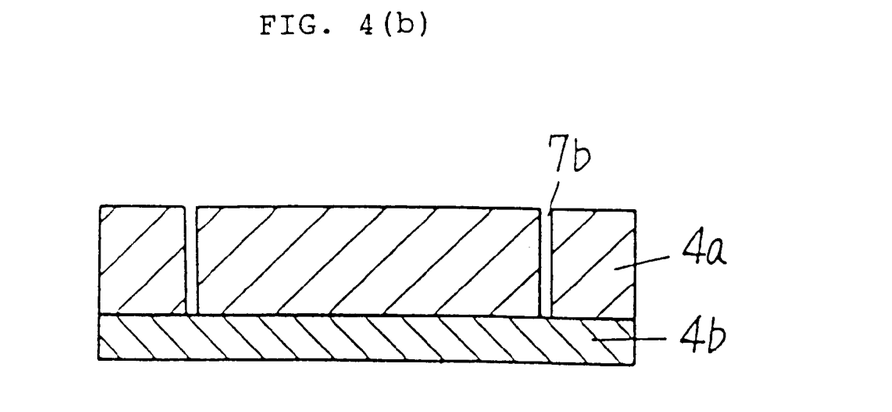
FIG. 4(b) is a sectional view for showing a substantial part of the central section.
Figure 5A:
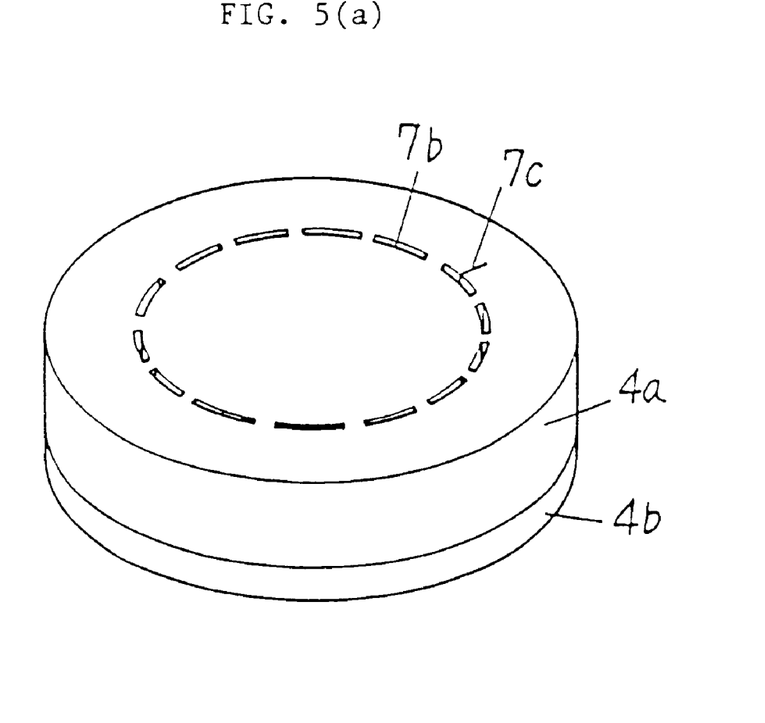
FIG. 5(a) is a perspective view for showing the protection layer provided with a vertical slit formed to face toward a circumferential direction at another part of the perforation notch of one of the other examples.
Figure 5B:
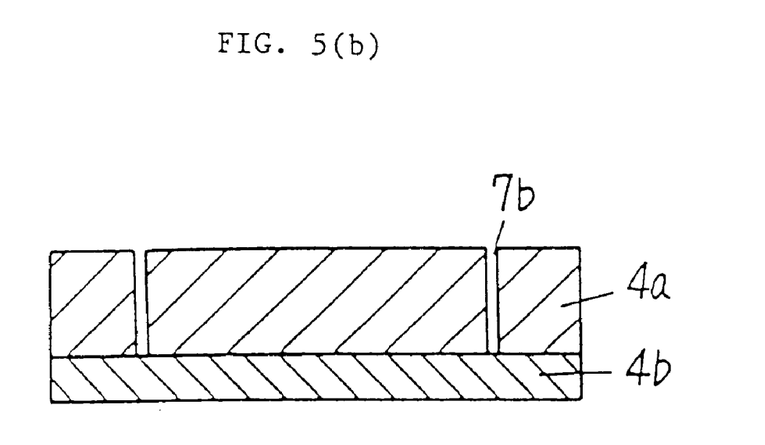
FIG. 5(b) is a sectional view for showing a substantial part of the central section.

Then, referring to FIGS. 3 to 5, a method for manufacturing a notch part 7 will be described as follows. FIG. 3(a) is a perspective view for showing a protection layer having a notch part formed by a die cut blade, FIG. 3(b) is a sectional view for showing a substantial part at the central section, FIG. 4(a) is a perspective view for showing the protection layer having a perforated notch section of one of the other examples of application, FIG. 4(b) is a sectional view for showing a substantial part of the central section, FIG. 5(a) is a perspective view for showing the protection layer provided with a vertical slit formed to face toward a circumferential direction at another part of the perforation notch of one of the other examples and FIG. 5(b) is a sectional view for showing a substantial part of the central section.

The protection layer 4 is comprised of a notch forming layer 4a and a reinforcing layer 4b so as to prevent a leakage of physiologically active agents or additives and the like, apply a mechanical strength to them and further to prevent a breakage of them or the like. The notch forming layer 4a is cut with a die cut blade to form the notch part 7a. In this case, a through-pass location should not be present in the reinforcing layer 4b. In addition, in the case that a wall thickness of the protection layer 4 is made thick or a die-cutting machine has a high precision, the protection layer 4 may be formed of single kind of resin in place of laminated item. Further, as another method for manufacturing the notch part 7, this can be manufactured by laminating the notch forming layer 4a formed with the perforation notch part 7b into a desired shape and either a film or a sheet of synthetic resin having no perforation notch part 7b which can be heat sealed, as shown in FIG. 4. Additionally, it is also available to arrange the vertical slit 7c at the perforation notch 7b toward its circumferential direction in order to facilitate a peeling-off and removal of the protection layer 4 as shown in FIG. 5.

Operation of the plaster structure for iontophoresis of the preferred embodiment of the present invention constructed as described above will be described as follows.

Since the backing layer 2 and the protection layer 4 are sealingly adhered to each other until the plaster structure for iontophoresis is applied to a body of a patient, it is possible to prevent dispersion and leakage of the physiologically active agents and the additives from the medicinal substance storing layer 1. In addition, when the plaster structure is applied to the patient, mere peeling-off of the liner layer 6 causes the section of the protection layer 4 enclosed by the notch part 7 to be easily removed together with the liner layer 6 and enables the releasing passage 8 for the physiologically active agents to be formed. Since the protection layer 4 and the adhesive agent layer 5 around the peripheral edge of the notch part 7 are left as they are, they can be closely contacted with a disease part in a body. Since the adhesive agent layer 5 is not left in the releasing passage of the physiologically active agents, when the physiologically active agents is to be released, the physiologically active agents or additives and the adhering agent can prevent their mutual action from each other.

Further, the notch part 7 of the protection layer 4 may be formed at a side opposite to that of the preferred embodiment shown in FIG. 3, i.e. at a side opposite to that of the medicinal substance storing layer 1. In the case that the protection layer 4 has a thick wall or it is made of synthetic resin having a high mechanical strength, the protection layer 4 at the outer circumference of the notch part 7, is held by the backing layer 2, so that a peeling-off force when the liner layer 6 is to be peeled off may easily separate to cut the protection layer 4 inside the notch to form the releasing passage 8 for the physiologically active agents.

Preferred Embodiment 2

Figure 6:
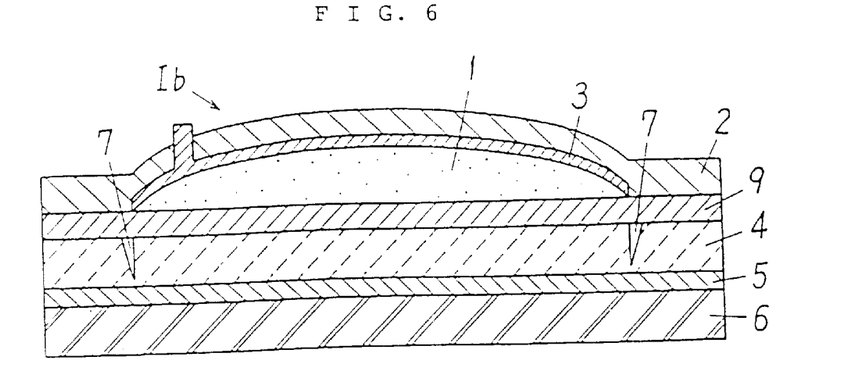
FIG. 6 is a central longitudinal view in section for showing a substantial part of the plaster structure for iontophoresis in a second preferred embodiment of the present invention.

FIG. 6 is a longitudinal section for showing a central section of a substantial part of the plaster structure for iontophoresis in a second preferred embodiment of the present invention.

A feature of the plaster structure Ib for iontophoresis of the second preferred embodiment differing from the plaster structure Ia for iontophoresis of the first preferred embodiment consists in the fact that the spacer film layer 9 is formed to be contacted with the lower (second) surface of the medicinal substance storing layer 1 and the lower (second) surface of the backing layer 2 of at least the peripheral part of the medicinal substance storing layer 1. A thickness of the spacer film layer 9 is 1 to 500 $\mu$m and preferably 10 to 200 $\mu$m. There is an opportunity that as the thickness becomes thinner than 10 $\mu$m, too much amount of releasing of physiologically active agent and a too high irritation against skin are applied, and in turn as the thickness exceeds 200 $\mu$m, a releasing amount of the physiologically active agents is too less and an administering time more than that required is needed, so that they are not preferable. A rate of void in the spacer film layer 9 and a size of fine hole can be set optionally in response to an object of controlling operation for the releasing for every physiologically active agents enclosed in the medicinal substance storing layer 1. Although the method for adhering the backing layer 2, the spacer film layer 9 and the protection layer 4 is not restricted, in general, it is preferable to apply a permanent heat seal which can not be peeled off so as to prevent a leakage of the physiologically active agents or additives.

As described above, in accordance with the preferred embodiment of the present invention, since the spacer film layer 9 is provided between the medicinal substance storing layer 1 and the protection layer 4, it is possible to control the administering of the physiologically active agents to the most-suitable administering amount. In addition, since the administering amount of the physiologically active agents can be adjusted, it is possible to release the skin irritation.

Preferred Embodiment 3

Figure 7:
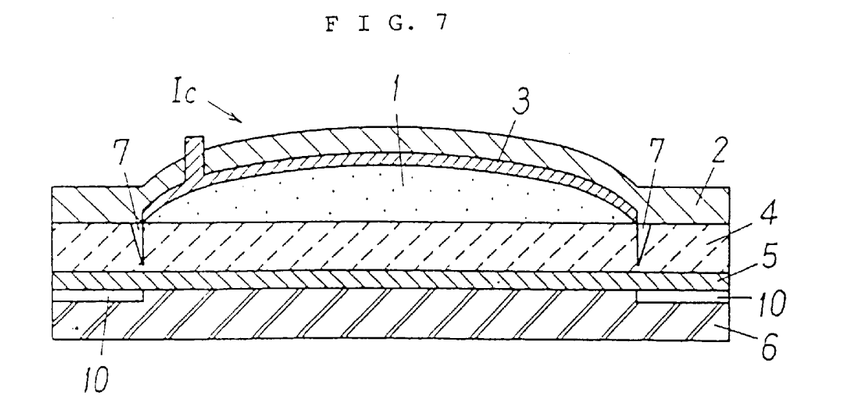
FIG. 7 is a central longitudinal view in section for showing a substantial part of the plaster structure for iontophoresis in a third preferred embodiment of the present invention.

FIG. 7 is a longitudinal view in section for showing a central part of a substantial section of the plaster structure for iontophoresis in the third preferred embodiment of the present invention.

A feature of the plaster structure Ic for iontophoresis of the third preferred embodiment different from the plaster structure Ia for iontophoresis of the first preferred embodiment consists in a presence of the removal processing part 10 at the peripheral edge part where a part corresponding to a broken and removed section of the protection layer 4 at the surface at the side of the adhesive agent layer 5 of the liner layer 6 is removed.

Since the present preferred embodiment is constructed as above, only the part enclosed by the notch part 7 of the protection layer 4 shows an increased adhering force between the liner layer 6 and the adhesive agent layer 5 and the removal processing part 10 shows a weak adhering power. With such an arrangement as above, the protection layer 4 can be spaced apart quite easily by the notch part 7 and the releasing passage for the physiologically active agents can be formed.

Preferred Embodiment 4

Figure 8:
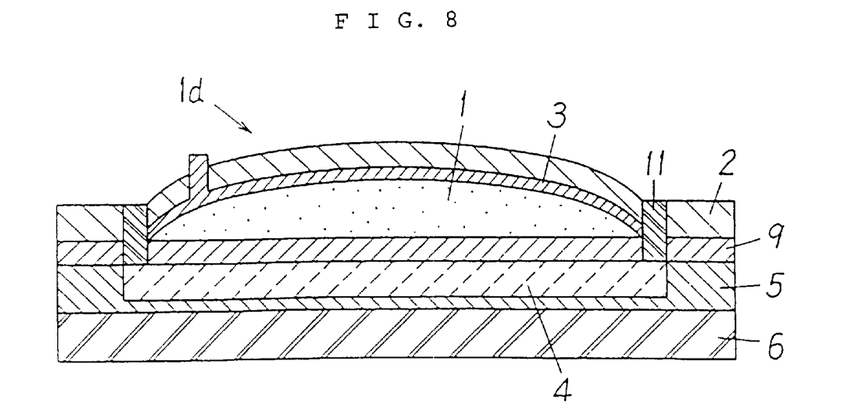
FIG. 8 is a central longitudinal view in section for showing a substantial part of the plaster structure for iontophoresis in a fourth preferred embodiment of the present invention.

FIG. 8 is a longitudinal section for showing a central part of a substantial section of the plaster structure for iontophoresis in a fourth preferred embodiment of the present invention.

A feature of the plaster structure Id of iontophoresis of the fourth preferred embodiment differing from the plaster structures Ia, Ib for iontophoresis of the first and second preferred embodiments consists in the fact that the backing layer 2 and the spacer film layer 9 enclosing the medicinal substance storing layer 1 and having an electrode 3 for iontophoresis are provided with a heat seal part 11 heat sealed at the circumferential part of the protection layer 4, the protection layer 4 has no notch part, the backing layer 2, the spacer film layer 9, the adhesive agent layer 5 and the liner layer 6 have a larger diameter than those of the medicinal substance storing layer 1 and the protection layer 4, and the protection layer 4 is formed to have a larger diameter than that of the heat seal part 11.

Since the present preferred embodiment is constructed as described above, it is possible to prevent dispersion and leakage of the physiologically active agents from the medicinal substance storing layer 1 until it is applied to the body of a patient and when it is applied to the patient, peeling of the liner layer 6 can be performed quite easily, the protection layer 4 can be removed together with the liner layer 6 so as to form the releasing passage for the physiologically active agents. At this time, since the adhesive agent is left only at the peripheral part of the protection layer 4, it is possible to prevent a bad influence caused by mutual action between the physiologically active agents or additives or the like and the adhesive agent when the physiologically active agents are released.

Industrial Applicability of the Invention

Since the present invention has been constructed as described above, it is possible to realize the plaster structure for iontophoresis having some superior effects described as follows.

(1) Since the medicinal substance storing layer is completely sealed by the backing layer and the protection layer to cause a sufficient restriction on leakage and dispersion of the physiologically active agents or additives being held, it is possible to perform a stable holding of them and also a stable administering of the physiologically active agents of initial designed amount.

(2) Since the protection layer is formed with a notch, a mere peeling-off of the liner layer enables the releasing passage for the physiologically active agents to be quite easily formed and a workability of an operating work to be remarkably improved.

(3) In addition, since the releasing passage for the physiologically active agents can be formed easily, accident such as leakage of the physiologically active agents or additives in the prior art can be prevented when the releasing passage for the physiologically active agents is formed and further a working efficiency can be improved.

(4) In the case that the spacer film layer is installed between the medicinal substance storing layer and the protection layer, it is possible to control a releasing amount of the physiologically active agents in addition to the effects described in the above (1) to (3).

(5) In the case that the circumferential edge of a part of the surface of the liner layer corresponding to a broken and removed section of the protection layer is removed or peeled, the removing or peeling-off part becomes a handle, so that a workability of forming the releasing passage for the physiologically active agents can be remarkably improved.

(6) Since the medicinal substance storing layer can be directly contacted with the disease part, the physiologically active agents can be administered without being influenced by the pressure-sensitive adhesive agent.

The plaster structure for iontophoresis of the present invention having some superior effects as described above normally realizes a superior healing effect to become a target by adhering it to a human body skin or mucous membrane and applying a voltage and so this is a medicinal substance which is quite useful in a medical industry.

What is claimed is:

1. A plaster structure for iontophoresis comprising:
   a medicinal substance storing layer which has electrical conductivity and contains physiologically active agents, said medicinal substance storing layer having first and second surfaces,
   a backing layer covering said first surface of said medicinal substance storing layer and being non-permeable against said physiologically active agents,
   an electrode installed in said backing layer,
   a protection layer having first and second surfaces, said first surface of said protection layer supporting said second surface of said medicinal substance storing layer and being non-permeable against said physiologically active agents,
   an adhesive agent layer having first and second surfaces, said first surface of said adhesive agent layer being laminated on said second surface of said protection layer, and
   a liner layer laminated on said second surface of said adhesive agent layer.

2. A plaster structure for iontophoresis according to claim 1, wherein said adhesive agent layer is comprised of a pressure-sensitive adhesive agent or gelation gluing agent.

3. A plaster structure for iontophoresis according to claim 1, wherein a spacer film layer which is permeable against said physiologically active agents is provided between said medicinal substance storing layer and said protection layer.

4. A plaster structure for iontophoresis according to claim 1, wherein said first surface of said protection layer comprises a contact surface and said contact surface is provided with an annular notch wherein said annular notch facilitates the removal of a portion of said protective layer and defines a removable section enabling access to said contact surface.

5. A plaster structure for iontophoresis according to claim 1, wherein said protection layer is comprised of two or more synthetic resin layers.

6. A plaster structure for iontophoresis according to claim 3, wherein said backing layer, said spacer film layer, said adhesive agent layer and said liner layer are formed to be larger in diameter than said medicinal substance storing layer and said protection layer, said backing layer being heat sealed around a peripheral edge part of said medicinal substance storing layer and said spacer film layer thereby forming a heat sealed section, and said protection layer is formed to be larger in perimeter than said heat sealed section.

7. A plaster structure for iontophoresis according to claim 2, wherein a spacer film layer which is permeable against said physiologically active agents is provided between said medicinal substance storing layer and said protection layer.

8. A plaster structure for iontophoresis according to claim 2, wherein said first surface of said protection layer is provided with an annular notch wherein said annular notch facilitates the removal of a portion of said protective layer and defines a removable section enabling access to said contact surface.

9. A plaster structure for iontophoresis according to claim 2, wherein said protection layer is comprised of two or more synthetic resin layers.

10. A plaster structure for iontophoresis according to claim 3, wherein said protection layer is comprised of at least two synthetic resin layers.

11. A plaster structure for iontophoresis according to claim 4, wherein said protection layer is comprised of at least two synthetic resin layers.

12. A plaster structure for iontophoresis according to claim 7, wherein said protection layer is comprised of at least two synthetic resin layers.

13. A plaster structure for iontophoresis according to claim 8, wherein said protection layer is comprised of at least two synthetic resin layers.

14. A plaster structure for iontophoresis according to claim 5, further comprising a removal processing part, said removable processing part comprising a portion of said liner layer and said removable processing part is adapted to be broken and removed from a remaining portion of said liner layer.

15. A plaster structure for iontophoresis according to claim 8, further comprising a removal processing part, said removal processing part further comprising a portion of said liner layer and said removal processing part is adapted to be broken and removed from a remaining portion of said liner layer.

16. A plaster structure for iontophoresis according to claim 9, further comprising a removal processing part, said removal processing part further comprising a portion of said liner layer and said removal processing part is adapted to be broken and removed from a remaining portion of said liner layer.

17. A plaster structure for iontophoresis according to claim 10, further comprising a removal processing part, said removal processing part further comprising a portion of said liner layer and said removal-processing part is adapted to be broken and removed from a remaining portion of said liner layer.

18. A plaster structure for iontophoresis according to claim 11, further comprising a removal processing part, said removal processing part further comprising a portion of said liner layer and said removal processing part is adapted to be broken and removed from a remaining portion of said liner layer.

19. A plaster structure for iontophoresis according to claim 12, further comprising a removal processing part, said removal processing part further comprising a portion of said liner layer and said removal processing part is adapted to be broken and removed from a remaining portion of said liner layer.

20. A plaster structure for iontophoresis according to claim 13, further comprising a removal processing part, said removal processing part further comprising a portion of said liner layer and said removal processing part is adapted to be broken and removed from a remaining portion of said liner layer.

21. A plaster structure for iontophoresis according to claim 5, wherein said backing layer, said spacer film layer, said adhesive agent layer and said liner layer are formed to be larger in diameter than said medicinal substance storing layer and said protection layer, and said backing layer being heat sealed around a peripheral edge part of said medicinal substance storing layer and said spacer film layer thereby forming a heat sealed section, and said protection layer is formed to be larger in perimeter than said heat sealed section.

22. A plaster structure for iontophoresis according to claim 7, wherein said backing layer, said spacer film layer, said adhesive agent layer and said liner layer are formed to be larger in diameter than said medicinal substance storing layer and said protection layer, and said backing layer being heat sealed around a peripheral edge part of said medicinal substance storing layer and said spacer film layer thereby forming a heat sealed section, and said protection layer is formed to be larger in perimeter than said heat sealed section.

23. A plaster structure for iontophoresis according to claim 9, wherein said backing layer, said spacer film layer, said adhesive agent layer and said liner layer are formed to be larger in diameter than said medicinal substance storing layer and said protection layer, and said backing layer being heat sealed around a peripheral edge part of said medicinal substance storing layer and said spacer film layer thereby forming a heat sealed section, and said protection layer is formed to be larger in perimeter than said heat sealed section.

24. A plaster structure for iontophoresis according to claim 10, wherein said backing layer, said spacer film layer, said adhesive agent layer and said liner layer are formed to be larger in diameter than said medicinal substance storing layer and said protection layer, and said backing layer being heat sealed around a peripheral edge part of said medicinal substance storing layer and said spacer film layer thereby forming a heat sealed section, and said protection layer is formed to be larger in perimeter than said heat sealed section.

25. A plaster structure for iontophoresis according to claim 12, wherein said backing layer, said spacer film layer, said adhesive agent layer and said liner layer are formed to be larger in diameter than said medicinal substance storing layer and said protection layer, and said backing layer being heat sealed around a peripheral edge part of said medicinal substance storing layer and said spacer film layer thereby forming a heat sealed section, and said protection layer is formed to be larger in perimeter than said heat sealed section.

26. A plaster structure for iontophoresis according to claim 4, further comprising a removal processing part, said removal processing part further comprising a portion of said liner layer and said removal processing part is adapted to be broken and removed from a remaining portion of said liner layer.

* * * * *